(12) United States Patent
Prisco et al.

(10) Patent No.: US 7,899,578 B2
(45) Date of Patent: *Mar. 1, 2011

(54) MEDICAL ROBOTIC SYSTEM WITH SLIDING MODE CONTROL

(75) Inventors: Giuseppe M. Prisco, Mountain View, CA (US); David Q. Larkin, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 20 days.

This patent is subject to a terminal disclaimer.

(21) Appl. No.: 12/247,346

(22) Filed: Oct. 8, 2008

(65) Prior Publication Data

US 2009/0099692 A1    Apr. 16, 2009

Related U.S. Application Data

(63) Continuation of application No. 11/613,962, filed on Dec. 20, 2006, now Pat. No. 7,453,227.

(60) Provisional application No. 60/751,839, filed on Dec. 20, 2005.

(51) Int. Cl.
*B25J 13/08* (2006.01)

(52) U.S. Cl. .......................................... 700/254; 901/2

(58) Field of Classification Search ..............................
318/568.11–568.22, 610, 619, 621, 632, 318/573, 609; 600/101, 160, 407, 429; 606/1, 606/130; 700/245, 251, 254, 257, 260, 264
See application file for complete search history.

(56) References Cited

U.S. PATENT DOCUMENTS

| | | | |
|---|---|---|---|
| 5,231,693 A | | 7/1993 | Backes et al. |
| 5,371,669 A | * | 12/1994 | Venkataraman et al. ....... 700/40 |
| 5,377,106 A | * | 12/1994 | Drunk et al. .................. 701/25 |
| 5,993,338 A | * | 11/1999 | Kato et al. ..................... 474/12 |
| 6,424,885 B1 | | 7/2002 | Niemeyer et al. |
| 6,459,926 B1 | * | 10/2002 | Nowlin et al. ............... 600/429 |
| 6,507,997 B2 | * | 1/2003 | Kawai et al. .................. 29/833 |
| 6,587,750 B2 | | 7/2003 | Gerbi et al. |

(Continued)

OTHER PUBLICATIONS

Bartolini Giorgio et al., "Hybrid Second Order Sliding Mode Control of Constrained Manipulators with Frictional Contact," Proceedings of the 40th IEEE Conference on Decision and Control, 2001, pp. 1398-1403, vol. 2, IEEE.

(Continued)

*Primary Examiner*—Khoi Tran
*Assistant Examiner*—Rodney King

(57) ABSTRACT

A medical robotic system has a joint coupled to medical device or a slave manipulator or robotic arm adapted to hold and/or move the medical device for performing a medical procedure, and a control system for controlling movement of the joint according to user manipulation of a master manipulator. The control system includes at least one joint controller having a sliding mode control for reducing stick-slip behavior on its controlled joint during fine motions of the joint. The sliding mode control computes a distance to a sliding surface, computes a reaching law gain, and processes the distance and reaching law gain to generate a sliding mode control action that is in absolute value less that a maximum desired feedback control action. The sliding mode control action is then further processed to generate a feedback torque command for the joint motor.

14 Claims, 10 Drawing Sheets

U.S. PATENT DOCUMENTS

| | | | |
|---|---|---|---|
| 6,671,581 | B2 | 12/2003 | Niemeyer et al. |
| 6,798,611 | B1* | 9/2004 | Romano et al. .......... 360/78.09 |
| 6,839,612 | B2 | 1/2005 | Sanchez et al. |
| 6,879,880 | B2 | 4/2005 | Nowlin et al. |
| 6,963,792 | B1 | 11/2005 | Green |
| 7,087,049 | B2 | 8/2006 | Nowlin et al. |
| 2002/0120363 | A1* | 8/2002 | Salisbury et al. ............ 700/254 |
| 2003/0195664 | A1* | 10/2003 | Nowlin et al. ................ 700/260 |
| 2003/0216836 | A1* | 11/2003 | Treat et al. .................. 700/245 |
| 2007/0167702 | A1 | 7/2007 | Hasser et al. |

OTHER PUBLICATIONS

Bhat, Sanjay P. et al., "Continuous Finite-Time Stabilization of the Translational and Rotational Double Integrators," IEEE Transactions on Automatic Control, 1998, IEEE Transactions on Automatic Control, pp. 678-682, vol. 43, No. 5, IEEE.

Buttolo, Pietro et al., "Sliding Control of Force Reflecting Teleoperation: Preliminary Studies," PRESENCE, 1994, vol. 3, No. 2, pp. 158-172.

Fiene, Jonathan et al., "Toward High-Speed Switching Motor Control for Human-Interactive Robotics," Proceedings of the 2005 IEEE International Conference on Robotics and Automation, 2005, pp. 1489-1494, IEEE.

Fridman, L., "The Problem of Chattering: an Averaging Approach," Lecture Notes in Control and Information Sciences, vol. 247, pp. 363-386, 1999, Springer Verlag, Berlin/Heidelberg.

Golo, Goran et al., "Robust discrete-time chattering free sliding mode control," Systems and Control Letters, 2000, pp. 19-28, vol. 41, No. 1, Elsevier.

Guldner, J. et al., "The chattering problem in sliding mode systems," 12$^{th}$ International Symposium on Mathematical Theory of Networks and Systems, 2000, Perpignan, France, 8 pages.

Hung, John Y. et al, "Variable Structure Control: A Survey," IEEE Transactions on Industrial Electronics, 1993, pp. 2-22, vol. 40 No. 1, IEEE.

Jezernik, Karel et al., "Observer Based Sliding Mode Control of Robotic Manipulator," Robotica, vol. 12, 1994, pp. 1-14.

Kikuuwe, Ryo et al., "Proxy-Based Sliding Mode Control for Accurate and Safe Position Control," IEEE International Conference on Robotics and Automation, 2006, pp. 25-30, IEEE.

Kwon, Dong-Soo et aL, "Design of a Teleoperation Controller for an Underwater Manipulator," IEEE International Conference on Robotics and Automation, 2000, pp. 3114-3119, vol. 4, IEEE.

Lee, Seok-Beom et al., "Sliding Mode Compensation of Dry Friction," Proceedings of the 1996 IEEE International Conference on Control Applications, 1996, pp. 809-813, IEEE.

Levant, Arie et al., "Robustness issues of 2-sliding mode control," IEE Control Engineering Series, Issue 66, 2004, 37 pages, Peter Peregrinus Ltd.

Monsees, Govert et al., "Adaptive Switching Gain for a Discrete-Time Sliding Mode Controller, Proceedings of the American Control Conference," 2000, pp. 1639-1643, vol. 3, IEEE.

Monsees, Govert, "Discrete-Time Sliding Mode Control," 2002, 182 pages. Internet: http://www.dcsc.tudelft.nl/Research/PublicationFiles/publication-5390.pdf.

Newman, W.S., "Robust Near Time-Optimal Control," IEEE Transactions on Automatic Control, vol. 35, No. 7, pp. 841-844, 1990, IEEE.

Nguyen, Tri V.M. et al., "A Chattering-Free Variable Structure Controller for Tracking of Robotic Manipulators," Proceedings of the 2003 Australasian Conference on Robotics and Automation, 2003, pp. 1-6.

Sabanovic, Asif et al., "Chattering Free Sliding Modes in Robotic Manipulators Control," IEEE/RSJ International Conference on Intelligent Robots and System, 1993, vol. 2, pp. 1-23, IEEE.

Sane, Harshad S. et al., "Modified Sliding Mode Control and its Application to Electrostatically Controlled Dual-Axis Micromirrors," Proceedings of the 2004 American Control Conference, 2004, vol. 3, pp. 1934-1939, IEEE.

Shi, Jingxin et al., "Chatter Free Variable Structure Perturbation Estimator on the Torque Control of Flexible Robot Joints with Disturbance and Parametric Uncertainties," Proceedings of the 1996 IEEE IECON 22nd International Conference on Industrial Electronics, Control, and Instrumentation, 1996, vol. 1, pp. 238-243, IEEE.

Song, Gangbing et al., "A Comparative Study of Conventional Nonsmooth Time-Invariant and Smooth Time-Varying Robust Compensators," IEEE Transactions on Control Systems Technology, 1998, vol. 6, No. 4, pp. 571-576, IEEE.

Vertut, Jean et al., Robot Technology: Teleoperation and Robotics Evolution and Development, 1986, vol. 3A, 332 pages, English translation Prentice-Hall, Inc., Inglewood Cliffs, NJ, USA.

Wang, Jian et al., "Positioning and Tracking Control of an X-Y Table with Sliding Mode Control," 2003, 10 pages. Internet: http://people.mech.kuleuven.be/~jwang/paper/rocond_2003.pdf.

* cited by examiner

MEDICAL ROBOTIC SYSTEM WITH SLIDING MODE CONTROL

CROSS REFERENCE TO RELATED APPLICATIONS

This application is a continuation of U.S. application Ser. No. 11/613,962 filed Dec. 20, 2006, now U.S. Pat. No. 7,453,227, which claims priority from U.S. Provisional Application No. 60/751,839 filed Dec. 20, 2005, each of which is incorporated herein by reference.

FIELD OF THE INVENTION

The present invention generally relates to medical robotic systems and in particular, to a medical robotic system with sliding mode control.

BACKGROUND OF THE INVENTION

Medical robotic systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for minimally invasive surgery using such medical robotic systems is strong and growing.

Examples of medical robotic systems include the daVinci® Surgical System and the daVinci® S™ Surgical System from Intuitive Surgical, Inc., of Sunnyvale, Calif. Each of these systems includes a surgeon's console, a patient-side cart, a high performance three-dimensional ("3-D") vision system, and Intuitive Surgical's proprietary EndoWrist™ articulating instruments, which are modeled after the human wrist so that when added to the motions of the slave manipulator holding the surgical instrument, they allow at least a full six degrees of freedom of motion, which is comparable to or even greater than the natural motions of open surgery.

The daVinci® surgeon's console has a high-resolution stereoscopic video display with two progressive scan cathode ray tubes ("CRTs"). The system offers higher fidelity than polarization, shutter eyeglass, or other techniques. Each eye views a separate CRT presenting the left or right eye perspective, through an objective lens and a series of mirrors. The surgeon sits comfortably and looks into this display throughout surgery, making it an ideal place for the surgeon to display and manipulate 3-D intraoperative imagery.

The patient-side cart typically includes three or more slave manipulators for holding and manipulating medical devices such as surgical instruments and image capturing devices for performing and viewing a medical procedure at a surgical site within a patient. To manipulate these medical devices, the surgeon's console also includes master input devices which may be selectively associated with the medical devices (and the slave manipulators holding the medical devices) to manipulate them. Since the movements of the master input devices and their associated medical devices are scaled, this allows the surgeon to perform intricate medical procedures with greater ease than with conventional open surgery. It may also allow the surgeon to perform medical procedures that are not even feasible using conventional open surgery techniques.

During very fine movement of the instruments during a medical procedure, however, corresponding movement of mechanical elements (such as joints, gears, spools, and other driven elements) used in moving the instrument or the slave manipulator holding the instrument may require fine motion velocities that induce stick-slip behavior in their motion. Since such behavior at the mechanical element level may be translated to the movement of their corresponding surgical instruments, this behavior may significantly diminish the ability of the surgeon to efficiently perform any medical procedure requiring fine manipulation of tissue, surgical sutures, needles etc., such as for example during an anasthomosis. Possible root causes for this problem include the presence of static friction (stiction) and the associated increase of dynamic friction (Coulomb friction) for velocities in the fine motions range. Due to the non-linear nature of this problem, and the specific requirements of medical robotic surgery, simple gain adjustments and/or the addition of dithering to a conventional proportional-integral-derivative ("PID") joint controller may not acceptably resolve it.

OBJECTS AND SUMMARY OF THE INVENTION

Accordingly, one object of aspects of the present invention is a controller and method implemented in the controller for controlling a drivable mechanical element in a medical robotic system that reduces stick-slip behavior in velocity ranges corresponding to fine motions of the mechanical element.

Another object of aspects of the present invention is a controller and method implemented in the controller for controlling a drivable mechanical element in a medical robotic system without inducing audible chattering.

Still another object of aspects of the present invention is a controller and method implemented in the controller that exhibits over a population of medical robotic systems (and/or their selectively associated system components) conventionally desired control characteristics such as stability margins, responsiveness, and uniformity of performance (i.e., predictability) over the life of the medical robotic systems (and/or their selectively associated system components).

These and additional objects are accomplished by the various aspects of the present invention, wherein briefly stated, one aspect is a method for controlling a joint in a medical robotic system in response to user manipulation of a master input device, comprising: computing a distance from a sliding surface using at least a position error associated with commanded movement of the joint by the master input device; computing a sliding mode control action based at least in part on the distance to the sliding surface; and causing the joint to be moved at least partially in response to the sliding mode control action.

Another aspect is a medical robotic system comprising: a joint coupled to a medical device or a robotic arm adapted to move the medical device; and a controller configured to control movement of the joint by computing a distance from a sliding surface using the following equation:

$$\sigma = \lambda \cdot (QC - QL) + (VC - VL),$$

wherein $\sigma$ represents the distance, $\lambda$ is a parameter value, $(QC-QL)$ is a position error and $(VC-VL)$ is a velocity error associated with commanded movement of the joint; computing a sliding mode control action based at least in part on the distance to the sliding surface; and causing the joint to be moved at least partially in response to the sliding mode control action.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
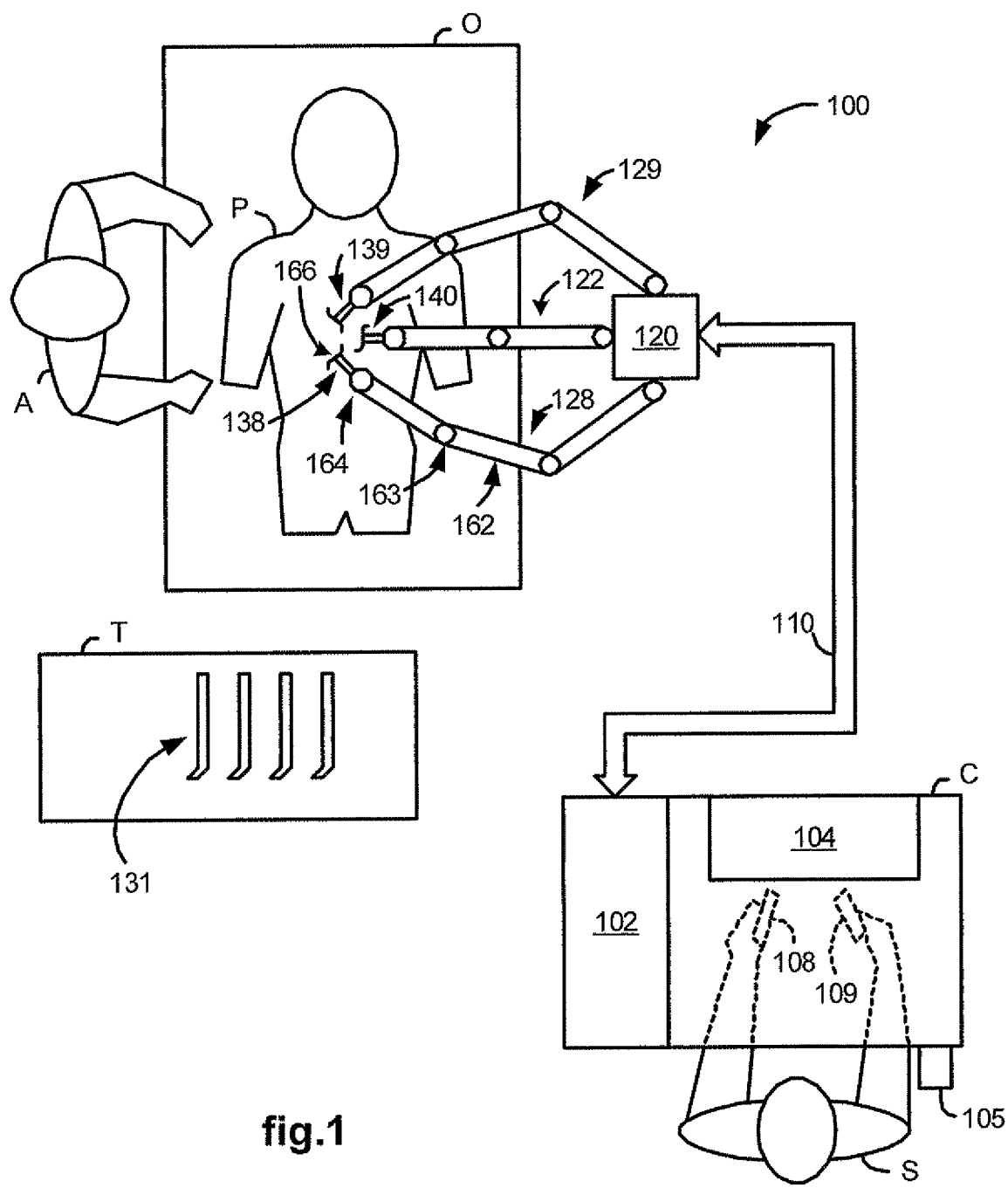
FIG. 1 illustrates a top view of an operating room employing a medical robotic system utilizing aspects of the present invention.

FIG. 1 illustrates, as an example, a top view of an operating room employing a medical robotic system. The medical robotic system in this case is a minimally invasive robotic surgical system 100 including a Console ("C") utilized by a Surgeon ("S") while performing a medical procedure, such as a diagnostic or surgical procedure, with assistance from one or more Assistants ("A"), on a Patient ("P") who is lying down on an Operating table ("O").

The Console includes a 3-D monitor 104 for displaying a 3-D image of a surgical site to the Surgeon, left and right manipulatable control devices 108, 109, a foot pedal 105, and a processor 102. The control devices 108, 109 may include any one or more of a variety of input devices such as joysticks, gloves, trigger-guns, hand-operated controllers, or the like. The processor 102 may be a dedicated computer integrated into the Console or positioned next or near to it, or it may be broken up into a number of processing or controller components that are distributed in a distributed processing fashion throughout the System 100.

The Surgeon performs a medical procedure by manipulating the control devices 108, 109 (also referred to herein as "master manipulators" and "master input devices") so that the processor 102 causes slave manipulators of their respectively associated robotic arm assemblies 128, 129 to manipulate their respective removably coupled surgical instruments 138, 139 (also referred to herein as "tools") accordingly, while the Surgeon views the surgical site in 3-D on the Console monitor 104 as it is captured by a stereoscopic endoscope 140.

Each of the tools 138, 139, as well as the Endoscope 140, is conventionally inserted through a tool guide (not shown) into the Patient so as to extend down to the surgical site through a corresponding minimally invasive incision such as Incision 166. The number of surgical tools used at one time and consequently, the number of robotic arms being used in the system 100 will generally depend on the medical procedure being performed and the space constraints within the operating room, among other factors. If it is necessary to change a tool being used during a procedure, the Assistant may remove the tool no longer being used from its robotic arm assembly, and replace it with another tool 131 from a Tray ("T") in the operating room.

So that the tools 138, 139 may be manipulated at the surgical site, they preferably each have a wrist mechanism including three joints (or other drivable mechanical elements such as gears, spools, etc.) for controlling the orientation of the wrist mechanism, and an additional joint (or other drivable mechanical element) controlling the eventual grip or other end effector joint of the tool. For additional details on such a tool wrist and end effector mechanism (and the mechanical elements and other linkages driving them), see, e.g., commonly owned U.S. Pat. No. 6,676,684 "Roll-Pitch-Roll-Yaw Surgical Tool", which is incorporated herein by this reference.

Each of the robotic arm assemblies 122, 128, 129 includes a slave manipulator and setup arms. The slave manipulators are robotically moved using motor controlled joints (also referred to herein as "active joints") in order to manipulate and/or move their respectively held medical devices. The setup arms may be manually manipulated by releasing normally braked joints (also referred to herein as "setup joints") to horizontally and vertically position the robotic arm assemblies 122, 128, 129 so that their respective medical devices may be inserted into their respective tool guides.

Preferably, the monitor 104 is positioned near the Surgeon's hands so that it will display a projected image that is oriented so that the Surgeon feels that he or she is actually looking directly down onto the operating site. To that end, images of the tools 138, 139 preferably appear to be located substantially where the Surgeon's hands are located.

The processor 102 performs various functions in the system 100. One important function that it performs is to translate and transfer the mechanical motion of control devices 108, 109 to their respective slave manipulators of robotic arm assemblies 128, 129 through control signals over bus 110 so that the Surgeon can effectively manipulate their respective tools 138, 139. Another important function is to implement various control system processes as described herein.

Although described as a processor, it is to be appreciated that the processor 102 may be implemented in practice by any combination of hardware, software and firmware. Also, its functions as described herein may be performed by one unit, or divided up among different components, each of which may be implemented in turn by any combination of hardware, software and firmware.

For additional details on the construction and operation of medical robotic systems such as described herein, see, e.g., commonly owned U.S. Pat. No. 6,493,608 "Aspects of a Control System of a Minimally Invasive Surgical Apparatus," and commonly owned U.S. Pat. No. 6,424,885 "Camera Referenced Control in a Minimally Invasive Surgical Apparatus," which are incorporated herein by reference.

Figure 2:
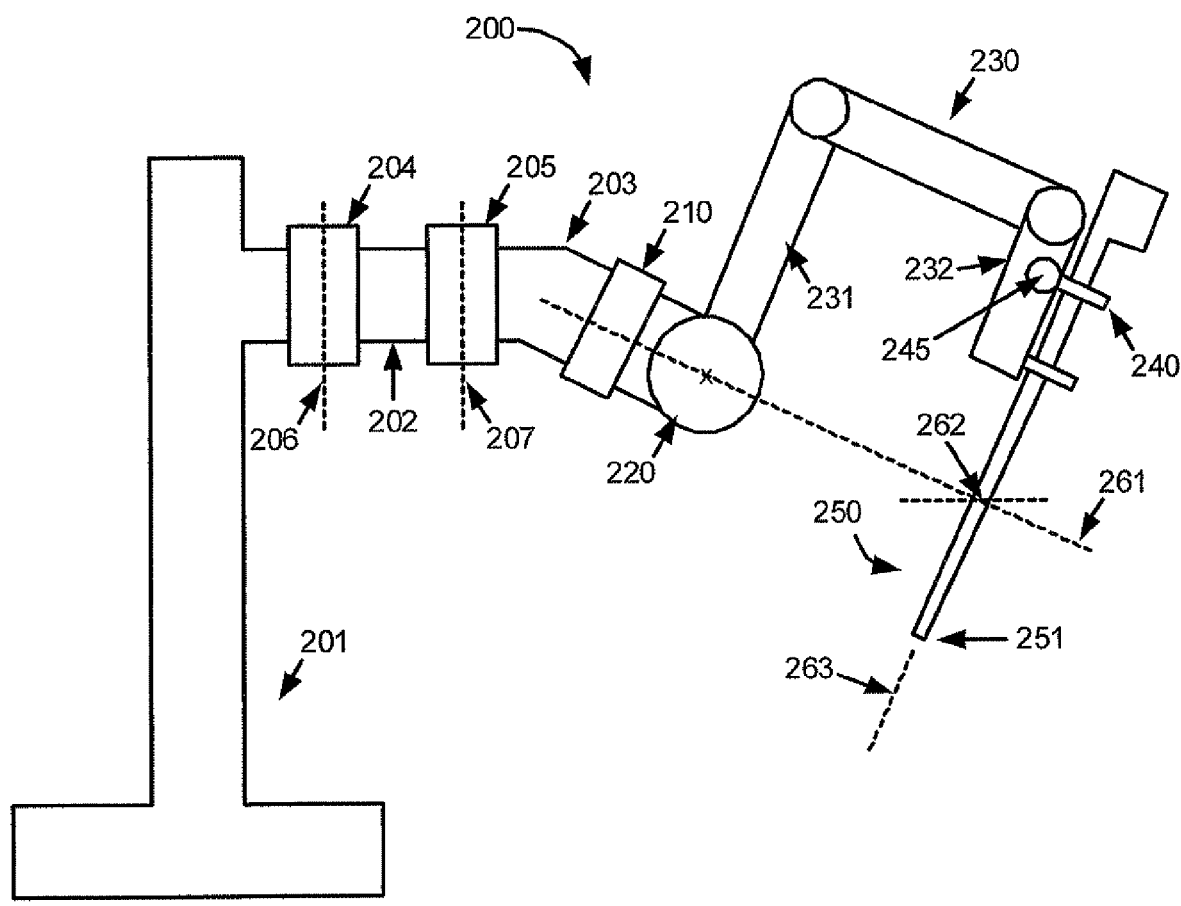
FIG. 2 illustrates a simplified side view of a robotic arm assembly that is usable with various aspects of the present invention.

FIG. 2 illustrates, as an example, a side view of a simplified (not necessarily in proportion or complete) robotic arm assembly 200 (which is representative of the robotic arm assemblies 128, 129) holding a surgical instrument 250 (which is representative of tools 138, 139) for performing a medical procedure. The surgical instrument 250 is removably held in tool holder 240. The robotic arm assembly 200 is mechanically supported by a base 201, which may be part of a patient-side movable cart or affixed to the operating table or ceiling. It includes links 202, 203 which are coupled together and to the base 201 through horizontal setup joints 204, 205.

The setup joints 204, 205 in this example are passive joints that allow manual positioning of the arm 200 when their brakes are released. For example, setup joint 204 allows link 202 to be manually rotated about axis 206, and setup joint 205 allows link 203 to be manually rotated about axis 207. The setup arm or portion of the robotic arm assembly 200 includes these setup joints.

Although only two links and two setup joints are shown in this example, more or less of each may be used as appropriate in this and other robotic arm assemblies in conjunction with the present invention. For example, although setup joints 204, 205 are useful for horizontal positioning of the arm 200, additional setup joints may be included and useful for limited vertical and angular positioning of the arm 200. For major vertical positioning of the arm 200, however, the arm 200 may also be slidably moved along the vertical axis of the base 201 and locked in position.

The robotic arm assembly 200 also includes three active joints driven by motors. A yaw joint 210 allows arm section 230 to rotate around an axis 261, and a pitch joint 220 allows arm section 230 to rotate about an axis perpendicular to that of axis 261 and orthogonal to the plane of the drawing. The slave manipulator of the robotic arm assembly 200 includes these active joints.

The arm section 230 is configured so that sections 231, 232 are always parallel to each other as the pitch joint 220 is rotated by its motor. As a consequence, the instrument 250 may be controllably moved by driving the yaw and pitch motors so as to pivot about the pivot point 262, which is generally located through manual positioning of the setup joints 204, 205 so as to be at the point of incision into the patient. In addition, an insertion gear 245 may be coupled to a linear drive mechanism (not shown) to extend or retract the instrument 250 along its axis 263.

Although each of the yaw, pitch and insertion joints or gears, 210, 220, 245, is controlled by an individual joint or gear controller, the three controllers are controlled by a common master/slave control system so that the slave manipulator of the robotic arm assembly 200 may be controlled through user (e.g., surgeon) manipulation of its associated master manipulator.

Figure 3:
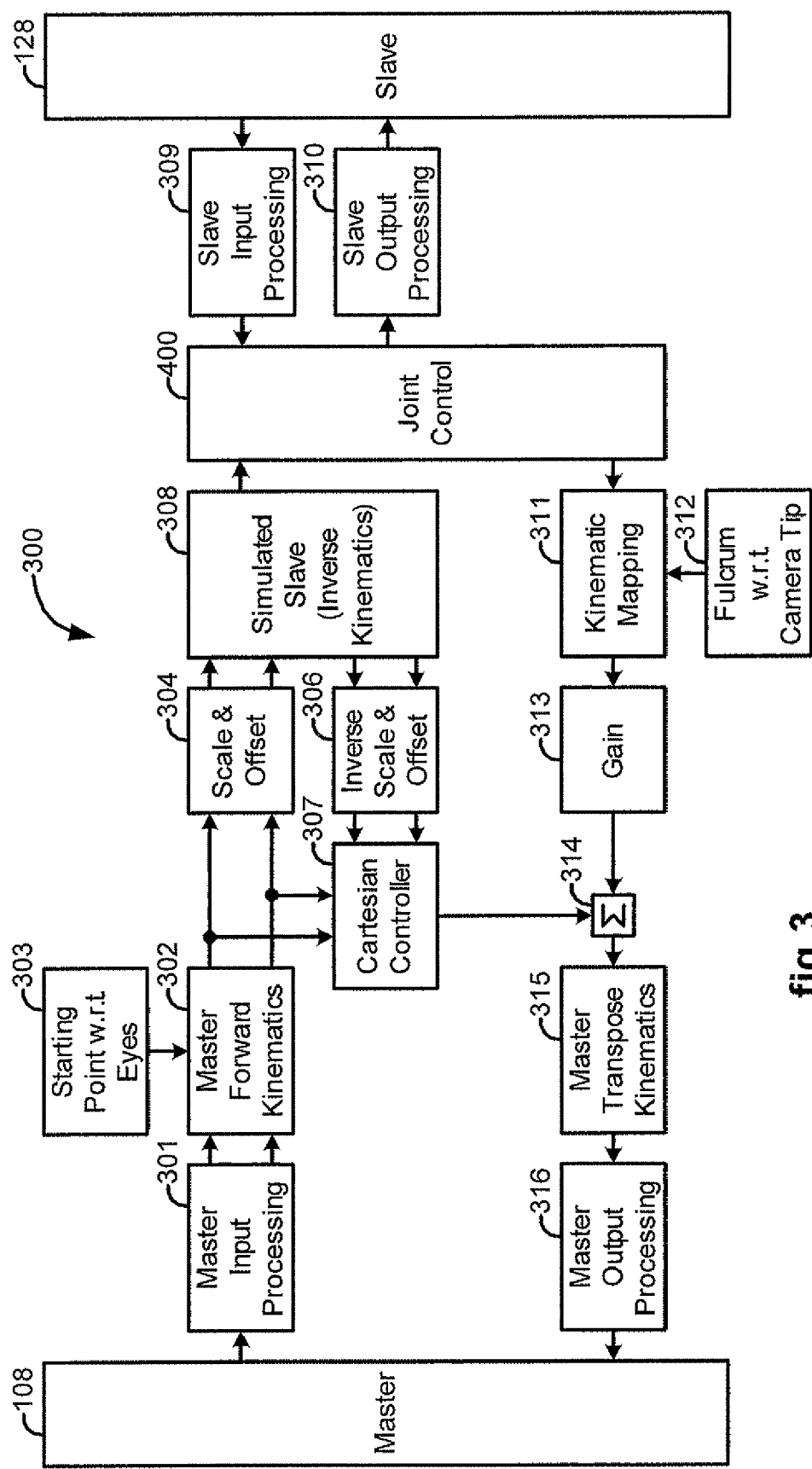
FIG. 3 illustrates a block diagram of a master/slave control system utilizing aspects of the present invention.

FIG. 3 illustrates, as an example, a block diagram of a master/slave control system 300 for controlling movement of the slave manipulator of the robotic arm assembly 128 and consequently, the position and orientation of its attached tool 138, as commanded by movement of the master manipulator 108 by a surgeon. A similar control system may also be provided for the slave manipulator of the robotic arm assembly 129 and its associated master manipulator 109.

Both the master and slave manipulators include a number of linkages connected by joints so as to facilitate multiple degrees-of-freedom movement. As the surgeon moves the master manipulator 108 from one position to another during the course of performing a surgical procedure, sensors associated with the master manipulator joints provide information indicating such command movement in master joint space, and sensors associated with the slave manipulator joints provide information indicating slave manipulator and consequently, tool 138 movement in slave joint space for feedback purposes. In order to better detect and control fine movements of their respective joints (e.g., in the target velocity range of 0.0005 to 0.01 radians per second at the joint, including the motion during the transition from zero velocity to the velocity in the target range), high resolution encoders are preferably used for the joint sensors.

A master input processing unit 301 receives the information of the master joint positions, which are sampled at the control system processing rate (e.g., 1300 Hz in the present example), from the master joint sensors in the master manipulator 108, and computes joint velocities from the sensed joint positions. A master forward kinematics processing unit 302 receives the master joint positions and velocities from the master input processing unit 301, transforms them from master joint space to corresponding positions and velocities of the master frame (i.e., the frame associated with the master manipulator 108) in Cartesian space relative to the eye reference frame (i.e., the reference frame associated with the position of the surgeon's eyes), using, for example, a Jacobian matrix and eye related information separately determined and provided in block 303.

A scale and offset processing unit 304 receives the Cartesian position and velocity commands from the master forward kinematics processing unit 302, scales the commanded movement according to a scale factor selected to perform the surgical procedure, and takes into account offsets to generate desired slave tool frame (i.e., the frame associated with the tool 138) positions and velocities. The scale adjustment is useful where small movements of the slave manipulator of the robotic arm assembly 128 are desired relative to larger movement of the master manipulator 108 in order to allow more precise movement of the slave tool 138 at the surgical site. The offsets, on the other hand, determine, for example, the corresponding position and/or orientation of an end effector frame (e.g., the frame associated with an end effector of the tool 138) in the camera reference frame (i.e., the frame associated with the distal tip of the endoscope 140) relative to a position and orientation of the master frame in the eye reference frame.

A simulated slave processing unit 308 receives desired slave tool frame position and velocity commands from the scale and offset processing unit 304, and limits the desired slave tool frame position, orientation and velocities, to assigned Cartesian Limits for instance to enforce correct and intuitive operation of the tool 138 by keeping it within its dexterous workspace. The simulated slave processing unit 308 generates simulated slave joint positions and velocities corresponding to the limited slave tool frame positions and velocities, while making sure that the generated slave joint positions and velocities do not exceed the actual slave joint's range of motion and maximum velocities (i.e., joint limits) even in the vicinity of kinematic singularities for the slave kinematics.

An inverse scale and offset processing unit 306 receives the simulated joint position and velocity commands from the simulated slave processing unit 308, and performs an inverse function to that of the scale and offset processing unit 304 on them. A Cartesian controller 307 receives as first inputs, the inputs to the scale and offset processing unit 304 and as second inputs, the outputs of the inverse scale and offset processing unit 306. The Cartesian controller 307 then generates an error signal as a difference of the first and second inputs, and a Cartesian force "$F_{CART}$" from the error signal such as with the following formula:

$$F_{CART} = K(\Delta x) + B(\Delta \dot{x}) \tag{1}$$

where "K" is a spring constant, "B" is a damping constant, "Δẋ" is the difference between the Cartesian velocity inputs to the Cartesian controller 307 and "Δx" is the difference between the Cartesian position inputs to the Cartesian controller 307. For an orientation error, a corresponding torque in Cartesian space is determined.

A master transpose kinematics processing unit 315 receives the Cartesian force $F_{CART}$ through a summation node 314, and generates a corresponding torque in joint space using, for example, the Jacobian transpose matrix and kinematic relationships associated with the master manipulator 108. A master output processing unit 316 receives the master torque signals from the master transpose kinematics processing unit 315, generates electrical currents corresponding to the master torque signals, and supplies the electrical currents to corresponding master joint motors of the master manipulator 108. As a result, a surgeon operating the master manipulator 108 feels the Cartesian force, $F_{CART}$, whenever the surgeon is commanding a position or velocity which exceeds system Cartesian or slave joint limits, or would result in a kinematic singularity condition for the slave manipulator of the robotic arm assembly 128.

As the master input processing unit 301 is receiving master joint positions from sensors in the master manipulator 108, a slave input processing unit 309 is also receiving slave joint positions from position sensors in the slave manipulator at the control system processing rate. A joint control unit 400 receives the slave joint positions from the slave input processing unit 309 and the simulated joint position commands provided from the simulated slave processing unit 308, and generates slave torque command signals for the slave joint motors and master torque feedback command signals for the master joint motors.

The slave torque command signals are generated by the joint control unit 400 so as to drive joints of the slave manipulator until feedback errors calculated in the joint control unit 400 zero out, as will be described in further detail in reference to FIG. 4. A slave output processing unit 310 receives the slave torque command signals from the joint control unit 400, converts them into appropriate electrical currents, and supplies the electrical currents to the joint motors of the slave manipulator so as to drive the motors accordingly.

The master torque feedback command signals are generated by the joint control unit 400 as a function of the slave joint position and velocity tracking errors so as to reflect forces being exerted against the tool 138 or its slave manipulator back to the master manipulator 108 so that they may be felt by the surgeon. A kinematic mapping unit 311 receives the master torque feedback command signals from the joint control unit 400, and generates the corresponding Cartesian force at the tip of the tool 138 relative to the camera frame of the endoscope 140 using the slave kinematic configuration and the previously calculated slave fulcrum (e.g., pivot point) position information provided in block 312.

A gain 313 adjusts the magnitude of the Cartesian force so as to ensure system stability while providing adequate force sensation to the surgeon. The gain adjusted Cartesian force is then passed through the summation node 314, and processed along with the Cartesian force provided by the Cartesian controller 307 through the Master transpose kinematics processing unit 315 and Master output processing 316 as previously described in reference to their processing of the Cartesian force provided by the Cartesian controller 307.

Additional details related to conventional aspects of the master/slave control system 300, such as the various reference frames referred to herein and the calculation of the surgeon eye related information provided in block 303 and the slave fulcrum information provided in block 312, which are based upon well-known mathematics, are described, for example, in previously incorporated by reference and commonly owned U.S. Pat. No. 6,424,885, "Camera Referenced Control in a Minimally Invasive Surgical Apparatus."

The joint control unit 400 includes a joint controller for each active joint of the slave manipulator of the robotic arm assembly 128 that is being controlled by the master/slave control system 300. In particular, where the slave manipulator 128 includes a yaw joint 210, a pitch joint 220, and an insertion axis gear 245, such as the robotic arm assembly 200 of FIG. 2, each of these joints or gears will have its own controller, as will each of the drivable mechanical elements for the tool wrist and end effector mechanisms.

Figure 4:
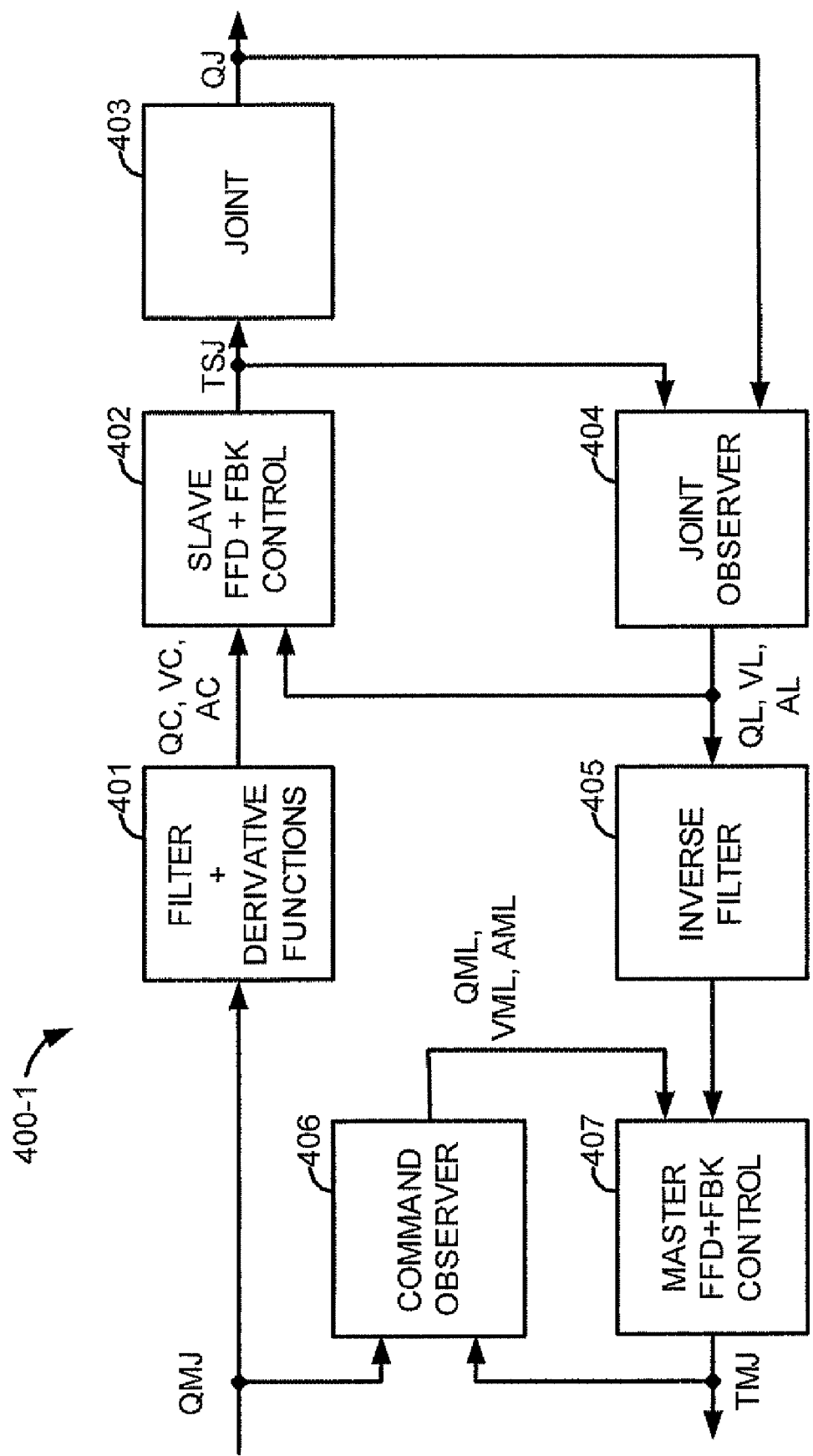
FIG. 4 illustrates a block diagram of a slave joint controller utilizing aspects of the present invention.

FIG. 4 illustrates, as an example, a block diagram of one such joint controller 400-1 (e.g., for controlling movement of either the yaw, pitch, or insertion joint or gear, 210, 220, 245, of the robotic arm assembly 200, or any one or more of several drivable mechanical elements for manipulating a tool wrist or end effector mechanism). To simplify the description herein and in the claims, the term "joint" is to be understood to include the joint drive train possibly including cables, pulleys, gears, spools, and any other drivable mechanical element that may be used in controlling degrees of freedom movement or other mechanical action associated with medical devices or the slave manipulators or robotic arms holding and/or moving the medical devices for performing medical procedures such as, for example, minimally invasive laparoscopic or endoluminal surgery.

First, an appropriate filter (plus derivative functions S and $S^2$) 401 is introduced into a forward path of the joint controller 400-1. The derivative functions are included, because the joint controller 400-1 employs a slave feedforward ("FFD") and feedback ("FBK") controller 402, which requires joint velocity and acceleration commands, as well as a joint position command. In order to better control fine movements of the joint, the controller 402 is preferably implemented so as to include a sliding mode controller, as described below. The filter used in block 401 is preferably a linear filter. The derivatives of a joint position command QMJ provided to the block 401 may be calculated after filtering of the joint position command QMJ, or they may be calculated before filtering of the joint position command QMJ. In the latter case, each of the joint position, velocity and acceleration commands may be individually filtered using the same or different filters. Preferably, the block 401 (i.e., the filter+derivative functions) is a digital state space balanced realization using standard techniques for its conversion from the continuous domain to the digital domain (e.g., Tustin method, Euler method, etc.). The joint position command QMJ is one of the simulated joint position commands from the simulated slave processing unit 308. The filtered joint position, velocity and acceleration commands QC, VC and AC are then provided to the slave controller 402.

Figure 10:
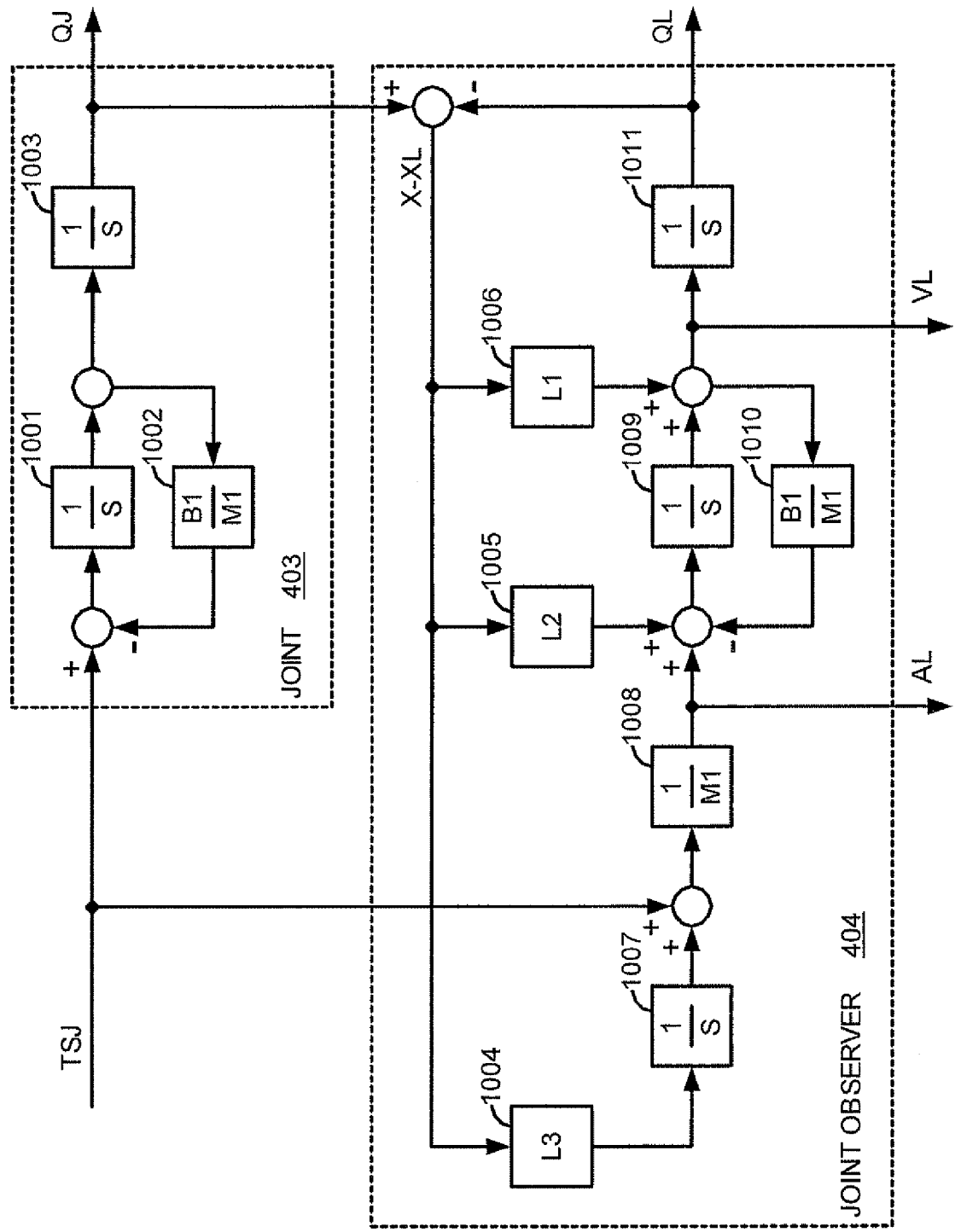
FIG. 10 illustrates a block diagram of a slave joint observer usable in a slave joint controller utilizing aspects of the present invention.

Since the filter in block 401 inserts delay into the joint controller 400-1, an inverse filter 405 is inserted in a feedback path to the master manipulator 108 to at least partially compensate for that delay. The inverse filter 405 is also preferably implemented in state space. In order to be the inverse of the forward path filter, it is configured so as to have a reciprocal transfer function. Thus, it is characterized as amplifying its incoming signal starting at the same cut-off frequency as the forward path filter so as to add phase lead instead of lag. Additional details on the construction and operation of such filters are described in commonly owned U.S. patent application Ser. No. 11/509,172 entitled "Robotic Surgical System with Joint Motion Controller Adapted to Reduce Instrument Tip Vibrations," filed Aug. 24, 2006, which is incorporated herein by this reference, To further enhance the accuracy (by reducing noise) and stability (by reducing loop delays) of the joint controller 400-1 and/or master/slave control system 300, a joint observer 404 is preferably inserted so as to estimate actual joint positions, velocities and accelerations, QL, VL and AL, using sensed position indications QJ from an encoder or sensor coupled to the slave joint, and torque commands TSJ provided to drive the slave joint motor. The slave joint motor, slave joint, and slave joint sensor are all included and indicated in this example by reference number 403. An example of the joint observer 404 is shown configured as a disturbance observer structure in FIG. 10, wherein the parameters B1 and M1 come from a rigid model of the slave joint dynamics 403, and the parameters L1, L2 and L3 are selected empirically through simulation and/or system calibration to provide good observer dynamics and accuracy. Note that the outputs of the joint observer 404 are provided to the inverse filter 405 and the slave controller 402 so that differences between corresponding of the joint position QC, velocity VC and acceleration AC commands, and estimated joint position QL, velocity VL and acceleration AL may be computed by the slave controller 402 in generating the torque command signal TSJ.

Figure 11:
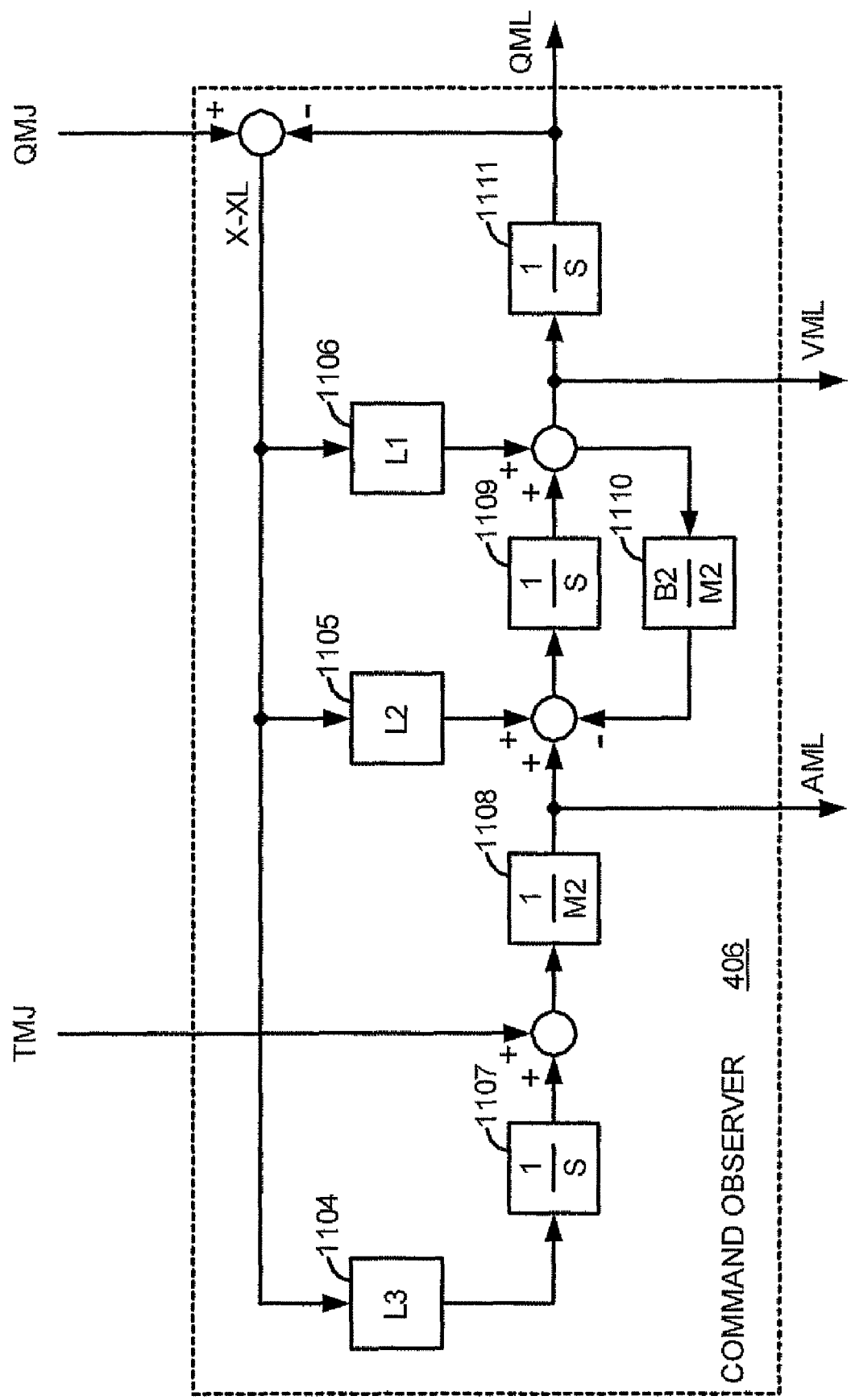
FIG. 11 illustrates a block diagram of a master command observer usable in a slave joint controller utilizing aspects of the present invention.

Also, to further enhance the accuracy and stability of the joint controller 400-1 and/or master/slave control system 300, a command observer 406 is preferably inserted so as to estimate joint position QML, velocity VML and acceleration AML commands using the joint position command QMJ and a torque feedback command TMJ. An example of the command observer 406 is shown configured as a disturbance observer structure in FIG. 11, wherein the parameters B2 and M2 come from a rigid model of the master dynamics, and the parameters L1, L2 and L3 are selected empirically through simulation and/or system calibration to provide good observer dynamics and accuracy (and may not necessarily be the same values as their counterparts in FIG. 10 even though they have the same parameter names). Note that the outputs of the command observer 406 are provided as negative values to the master controller 407 along with the outputs of the inverse filter 405, so that differences between corresponding of the inverse filtered, estimated joint positions QL, velocities VL and accelerations AL, and estimated joint position QML, velocity VML and acceleration AML commands may be calculated and used by the master controller 407 in generating the feedback torque TMJ.

Figure 6:
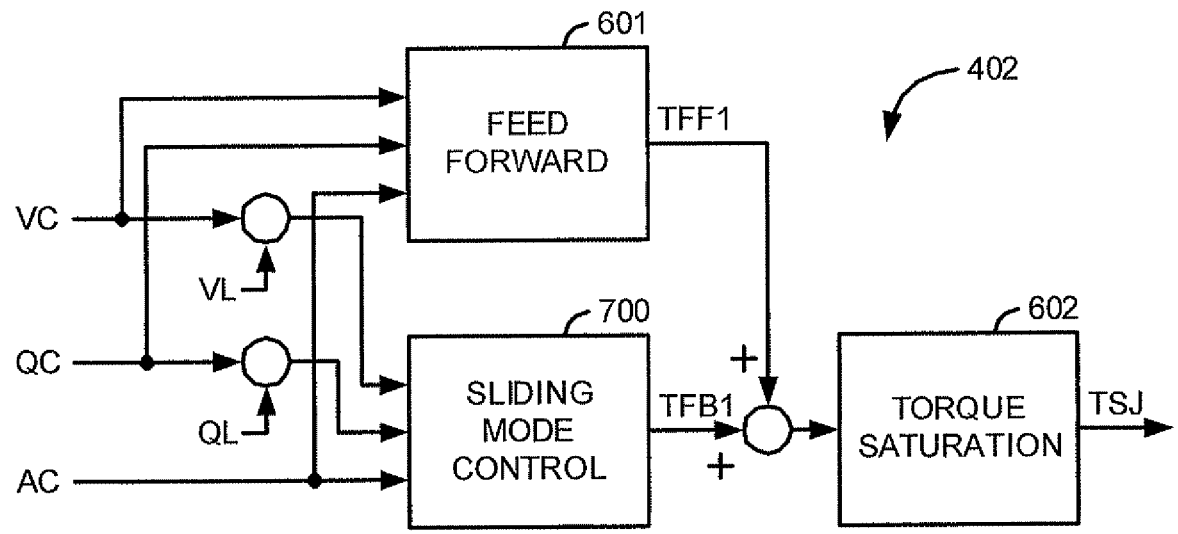
FIG. 6 illustrates a block diagram of a master feedforward and feedback controller usable in a slave joint controller utilizing aspects of the present invention.
Figure 5:
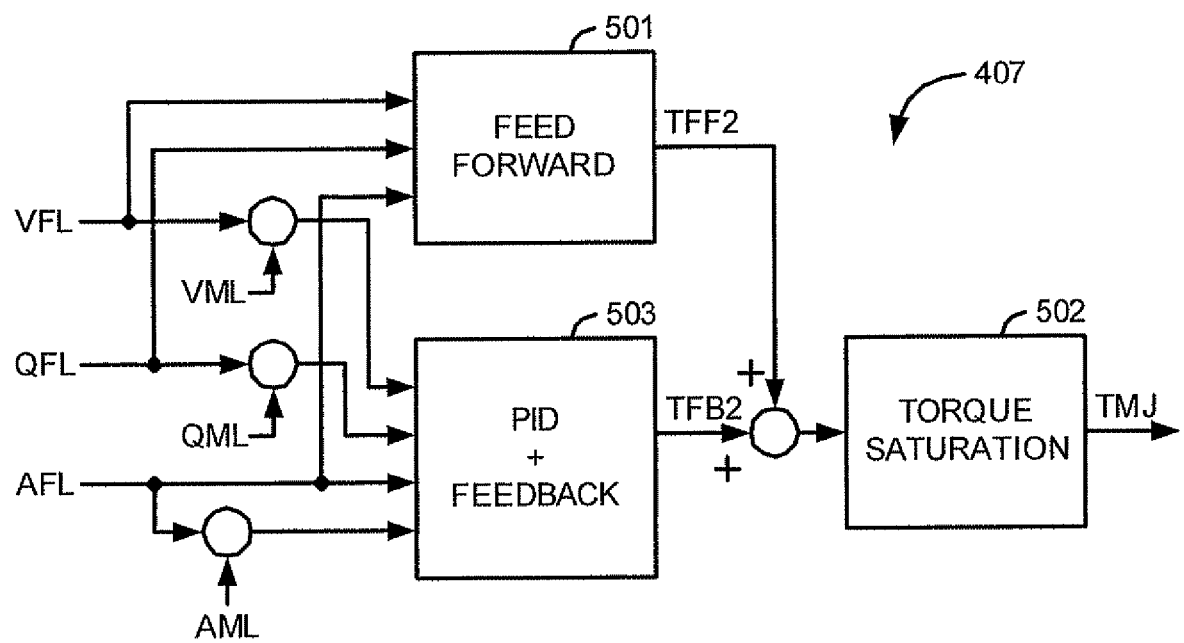
FIG. 5 illustrates a block diagram of a slave feedforward and feedback controller utilizing aspects of the present invention.

Referring to FIGS. 5 and 6, the master controller 407 may be similar in construction to the slave controller 402 with the exception that a proportional-integral-derivative ("PID") controller is used in lieu of the sliding mode control of the slave controller 402. Alternatively, they may be structurally identical so that the master controller 406 also provides improved stability margins, higher stiffness, and desirable return dynamics following large position errors associated with the master input device 108. The feedforward blocks 501, 601 respectively of the master and slave controllers 407, 402 preferably provide frictional and inertial resistance reduction for manual positioning of their respective slave manipulators, as described in commonly owned U.S. patent application Ser. No. 11/479,144 entitled "Control System for Reducing Internally Generated Frictional and Inertial Resistance to Manual Positioning of a Surgical Manipulator," filed Jun. 30, 2006, which is incorporated herein by this reference. The torque saturation blocks 502, 602 preferably limit commanded torque values in their respective controllers 407, 402 so as not to exceed maximum desired torque values for their respective motors.

Figure 7:
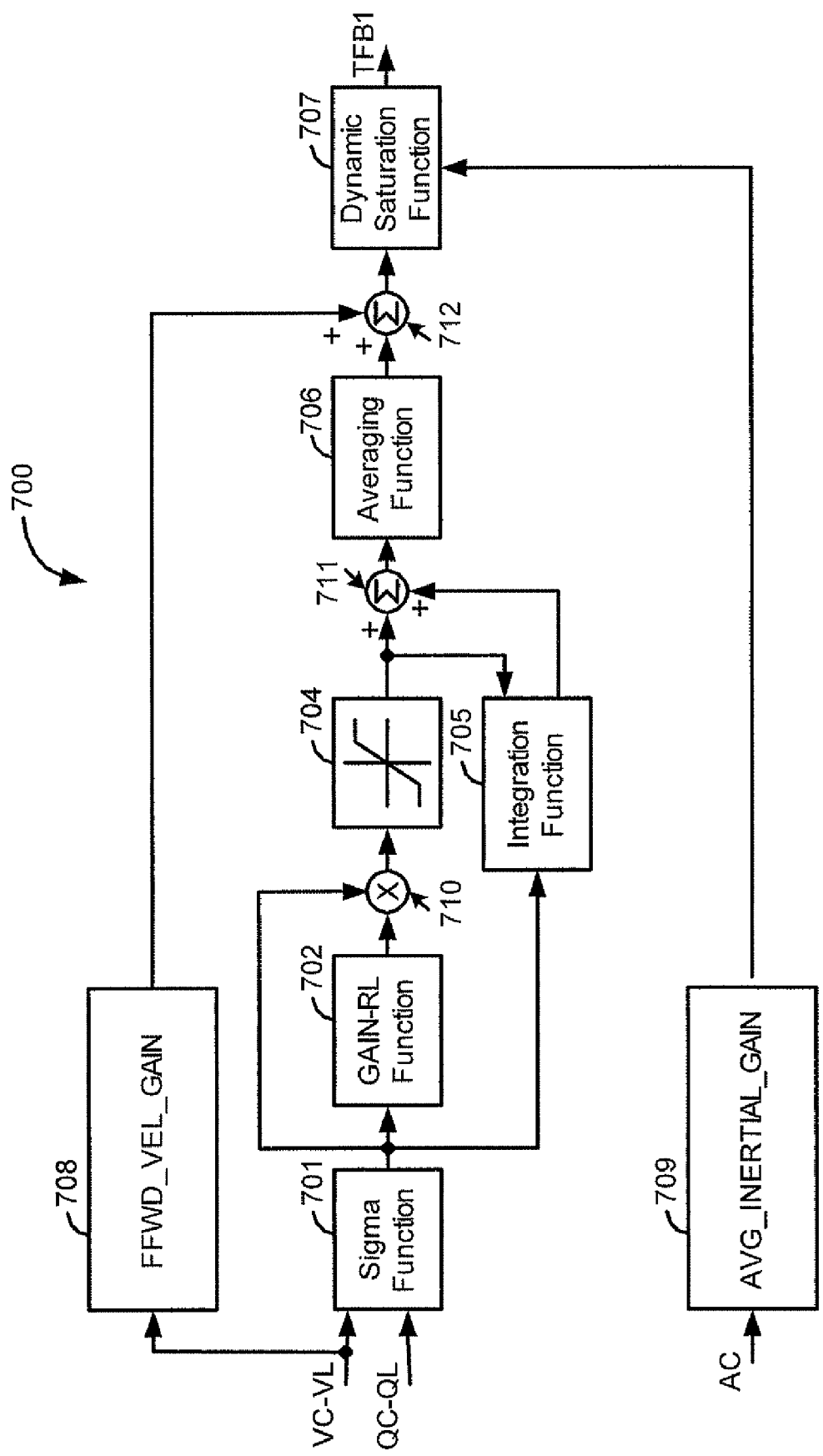
FIG. 7 illustrates a block diagram of a sliding mode control usable in the slave joint controller, utilizing aspects of the present invention.

FIG. 7 illustrates, as an example, a block diagram for the Sliding Mode Control 700, which is useful for reducing stick-slip behavior on its corresponding joint without chatter. A Sigma Function 701 receives position and velocity errors, (QC−QL) and (VC−VL), and computes a Sigma ($\sigma$) value which conceptually represents a distance in the joint state space to a sliding mode surface for sliding mode control purposes. For example, the joint state can be composed of, but is not necessarily limited to, the joint velocity and the joint position so as to define a two-dimensional joint state space.

The position error (QC−QL) may be calculated as the difference between the commanded joint position QC provided by the processing block 401 and the estimated joint position QL provided by the joint observer 404, and the velocity error (VC−VL) calculated as the difference between the commanded joint velocity VC provided by the processing block 401 and the estimated joint velocity VL provided by the joint observer 404. Alternatively, if a joint observer is not used, then the sensed joint position QJ may be simply used in lieu of the estimated joint position QL, and the estimated joint velocity VL may be simply calculated as the difference between sequentially sensed joint positions $(QJ(t_k), QJ(t_{k-1}))$ divided by the sampling period or interval $(T_s = t_k - t_{k-1})$.

The Sigma Function 701 may be any function suitable for sliding mode control of medical robotic systems, including a linear function such as:

$$\sigma = \lambda \cdot (QC-QL) + (VC-VL) \quad (2)$$

or alternatively, a quadratic function such as:

$$\sigma = \lambda \cdot (QC-QL) + (VC-VL)^2 \quad (3)$$

where "$\lambda$" is a parameter value selected or otherwise determined for the particular medical robotic system in which the sliding mode control is being applied.

A Reaching Law Function 702 applies the Sigma ($\sigma$) value to a reaching law in order to calculate a Gain "$GAIN_{RL}$" (or "GAIN-RL") which is used in the Sliding Mode Control 700 to drive the Sigma ($\sigma$) value to zero. The Reaching Law may be any monotonic mathematical function of the absolute value of Sigma ($\sigma$) that is suitable for sliding mode control of medical robotic systems, including a piece-wise linear reaching law such as:

$$GAIN_{RL} = Gmin + \frac{|\sigma|}{RS}, \text{ for } |\sigma| < Gmax \quad (4)$$

$$GAIN_{RL} = Gmax, \text{ for } |\sigma| \geq Gmax \quad (5)$$

or alternatively, a power rate reaching law such as:

$$GAIN_{RL} = \left(\frac{|\sigma|}{RS}\right)^v \quad (6)$$

where "RS" is a parameter value (i.e., the Reaching Size) selected or otherwise determined for the particular medical robotic system in which the sliding mode control is being applied, and "v" is an exponential value between 0 and 1, which is nominally set to 0.5 in this example.

In a first, basic digital implementation of the Integration Function 705, its Output (INT) is equal to the following:

$$INT(kT_s)=KI \cdot T_s \cdot (\text{sigma}+INT((k-1)T_s)) \quad (7)$$

where "$kT_s$" is the sampling instance, "$T_s$" is the sampling interval, KI is the Integrator Gain, sigma is the Sigma ($\sigma$) value, and "$INT((k-1)T_s)$" is the prior state of the Output (INT).

A Multiplication Node 710 multiplies the Sigma ($\sigma$) value by the Gain ($GAIN_{RL}$), a saturating block 704 limits the absolute value of the result to be less than a desired feedback Maximum Torque ($T_{MAX}$), and a Summing Node 711 adds the outputs of the saturating block 704 and the Integration Function 705 together to generate a Sliding Mode Control Action ($SMC_{ACT}$) command according to the following:

$$SMC_{ACT}=Sat(GAIN_{RL} \cdot \sigma)+INT(kT_s) \quad (8)$$

The Integration Function 705 may be modified in order to avoid generating a Sliding Mode Control Action ($SMC_{ACT}$) command which is greater than the Maximum Torque ($T_{MAX}$) for the motor that is being controlled. For such purpose, the integrator state "$INT(kT_s)$" is modified according to the improved equation:

$$INT(kT_s)'=Sat(INT(kT_s)+Sat(GAIN_{RL} \cdot \sigma))-Sat(GAIN_{RL} \cdot \sigma) \quad (9)$$

where "$Sat(u)$" is a function that saturates its input "u" when the absolute value of "u" is larger than the maximum allowed joint feedback torque Tmax.

Figure 8:
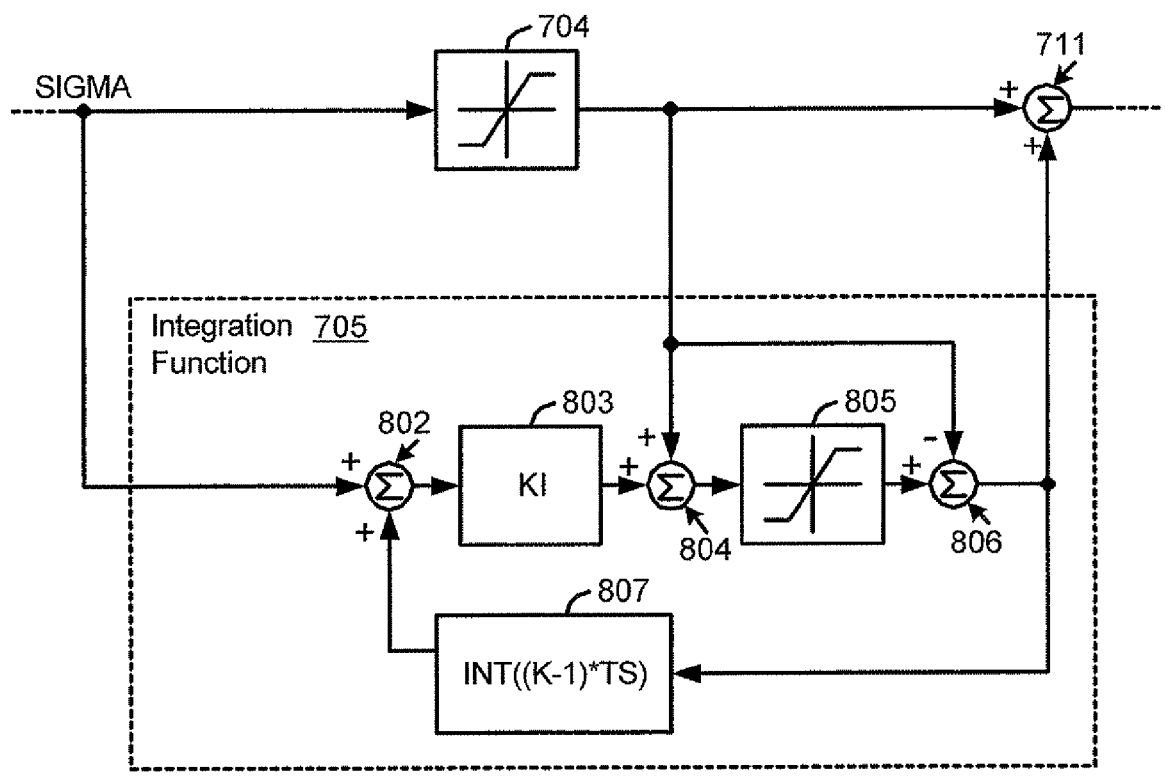
FIG. 8 illustrates a block diagram of an integration function usable in the sliding mode control, utilizing aspects of the present invention.

It can be appreciated that equation (9) guarantees that the integrator value INT is zeroed every time the Sliding Mode Control Action term "$GAIN_{RL} \cdot \sigma$" by itself saturates the maximum torque Tmax. Furthermore, it is easy to verify that at anytime, equations (7), (8) and (9) together ensure that the Sliding Mode Control Action never exceeds the maximum feedback torque Tmax. Although described as a two-step process, the "modified" integrator value may be determined directly using logic, for example, as shown in the block diagram of FIG. 8, where it is apparent that node 806 is zeroed when both limiters 704 and 805 saturate at the maximum torque value.

An Averaging Function 706 processes the Sliding Mode Control Action ($SMC_{ACT}$) command (recalculated using the modified output of the integrator "$INT(kT_s)$'" per equation (9)) to avoid abrupt changes over time of the control torque. As one example, the Averaging Function 706 may be implemented as a simple Low Pass Filter. Alternatively, the Averaging Function 706 could be skipped.

A Summing Node 712 sums the output of the Averaging Function 706 with the product of the Velocity Error, VC−VL, and a feedforward velocity gain ("FFWD_VEL_GAIN") provided in Velocity Error Gain Block 708. The output of the Summing Node 712 is then provided along with the product of the Acceleration Command AC and an Average Inertial Gain ("AVG_INERTIAL_GAIN") provided in Gain Block 709 to a Dynamic Saturation Function 707.

The Dynamic Saturation Function 707 places the following Dynamic Limit on the input which it receives from the Summing Node 712:

$$PDMAX=PDMAX\_STATIC+|AC \cdot AVG\_INERTIAL\_GAIN| \quad (10)$$

where PDMAX_STATIC is a static value for the joint feedback control torque suitably selected for the robotic system being controlled, and AVG_INERTIAL_GAIN is related to an equivalent joint inertia, averaged over the robotic arm configurations when the Sliding Mode Control 700 is being used to control a joint of a robotic arm assembly. The dynamic PDMAX in this case allows the Sliding Mode Control 700 to avoid the use of a noisy acceleration feedforward while improving the tracking performance by allowing a larger feedback torque when trajectories with high accelerations are commanded.

Figure 9:
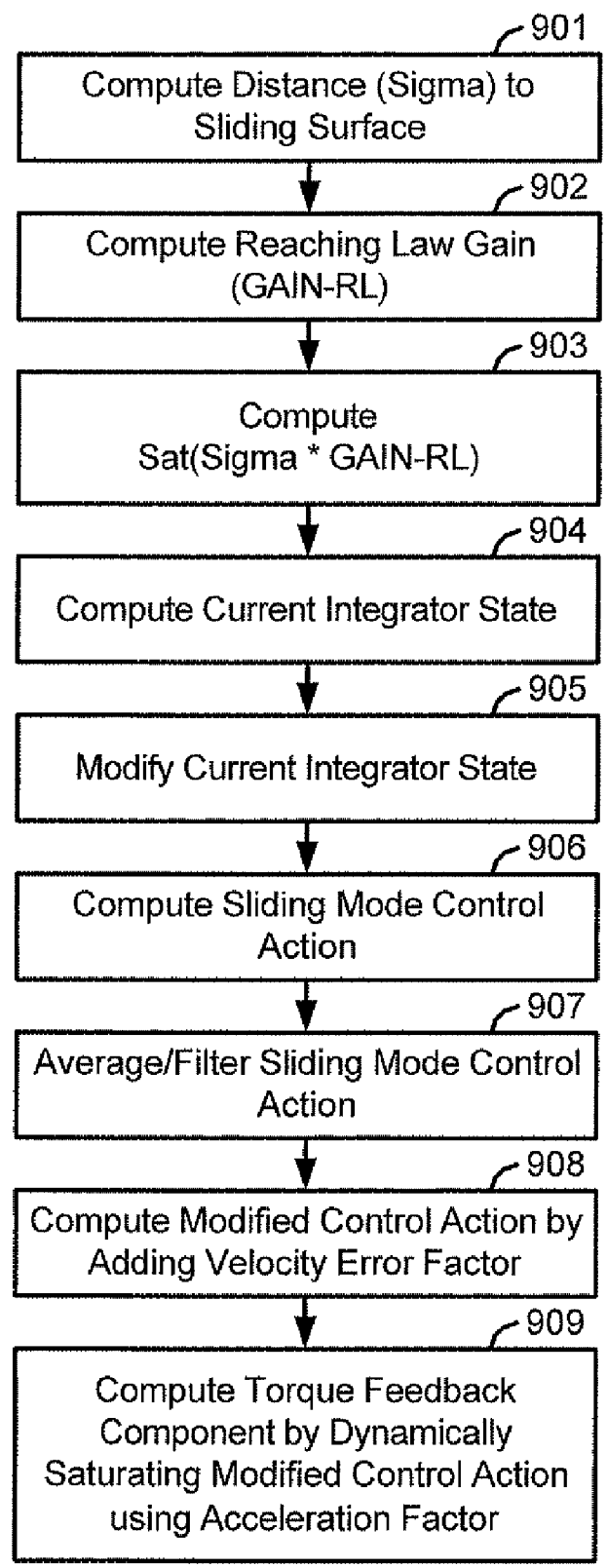
FIG. 9 illustrates a flow diagram of a sliding mode control method utilizing aspects of the present invention.

FIG. 9 illustrates, as an example, a flow diagram of a sliding mode control method implemented in the Sliding Mode Control 700. In 901, a distance "$\sigma$" to a sliding mode surface is computed using a linear function such as shown and described in reference to equation (2), or preferably, a quadratic function such as shown and described in reference to equation (3) above. In 902, a reaching law gain "$GAIN_{RL}$" is computed using a linear reaching law such as shown and described in reference to equations (4) and (5), or preferably, a power rate reaching law such as shown and described in reference to equation (6) above. In 903, the product of the reaching law gain "$GAIN_{RL}$" and the distance "$\sigma$" is computed and saturated to be in absolute value less than a control feedback action limitation. As an example of such a limitation, the limitation may be a maximum torque for the motor.

In 904, a current state "$INT(kT_S)$" of the integrator is computed using an integration function such as shown and described in reference to equation (7) above, and in 905, modified state "$INT(kT_s)$'" is computed as described in reference to equation (9) above using the saturated product calculated in 903.

In 906, a sliding mode control action "$SMC_{ACT}$" is computed by adding the modified state "$INT(kT_s)$'" of the integrator to the saturated product of the reaching law gain "$GAIN_{RL}$" and the distance $\sigma$, such as shown and described in reference to equation (8) above. In 907, the sliding mode control action "$SMC_{ACT}$" is averaged or otherwise filtered to avoid abrupt changes that would be produce unwanted mechanical vibrations. As an example, a simple low pass filter may be used for this purpose. This averaging step can also be skipped altogether especially in joints of high mechanical stiffness.

In 908, a summed value is computed by summing the filtered sliding mode control action computed in 907 with a velocity error feedforward factor derived from the commanded movement of the robotic arm. As an example, the velocity error factor may be the velocity error "(VC−VL)" multiplied by a feedforward velocity gain "FFWD_VELOCITY_GAIN1" such as shown and described in reference to FIG. 7. In 909, the summed value computed in 912 is dynamically limited using an acceleration factor derived from the commanded movement of the robotic arm. As an example, it may be dynamically limited as shown and described in reference to equation (10), where the acceleration factor is the absolute value of the product of the commanded acceleration "AC" and the gain "AVG_INERTIAL_GAIN".

Although the various aspects of the present invention have been described with respect to a preferred embodiment, it will be understood that the invention is entitled to full protection within the full scope of the appended claims.

We claim:

1. A method using sliding mode control for controlling movement of a joint in a medical robotic system in response to user manipulation of a master input device, comprising:

computing a distance from a sliding mode surface using the following equation: $\sigma=\lambda \cdot (QC-QL)+(VC-VL)$, wherein $\sigma$ represents the distance, $\lambda$ is a parameter value, (QC−QL) is a position error and (VC−VL) is a velocity error associated with commanded movement of the joint by the master input device;

computing a sliding mode control action using a non-linear function of the distance to the sliding mode surface; and causing the joint to be moved at least partially in response to the sliding mode control action.

2. The method according to claim 1, wherein the computation of the distance from the sliding surface employs a linear function using the position error and the velocity error.

3. The method according to claim 1, wherein the computation of the distance from the sliding mode surface employs a quadratic function using the position error and the velocity error.

4. The method according to claim 1, further comprising:
computing a reaching law gain using the distance,
wherein the computation of the sliding mode control action is based at least in part on a product of the reaching law gain and the distance.

5. The method according to claim 4, wherein the reaching law gain is a function of the absolute value of the distance.

6. The method according to claim 4, further comprising:
computing a current state for an integrator using a prior state of the integrator and the distance;
limiting the product of the reaching law gain and the distance to be less than a maximum control action; and
modifying the current state of the integrator using the limited product so as to limit a sum of the product and the current state of the integrator to be less than the maximum control action,
wherein the computation of the sliding mode control action is based at least in part on a sum of the limited product and the modified current state of the integrator.

7. The method according to claim 6, wherein the modification of the current state of the integrator comprises modifying the current state of the integrator so as to avoid exceeding a specification for a motor used to move the joint.

8. The method according to claim 1, further comprising:
filtering the sliding mode control action to avoid abrupt changes when causing the joint to be moved at least partially in response to the sliding mode control action,
wherein the joint is caused to be moved at least partially in response to the filtered sliding mode control action.

9. The method according to claim 1, further comprising:
dynamically limiting the sliding mode control action using an acceleration factor derived from the commanded movement of the joint,
wherein the joint is caused to be moved at least partially in response to the dynamically limited sliding mode control action.

10. A medical robotic system comprising:
a joint coupled to a medical device or a robotic arm adapted to move the medical device; and
a controller configured to use sliding mode control to control movement of the joint by computing a distance from a sliding mode surface using the following equation:

$$\sigma = \lambda \cdot (QC-QL) + (VC-VL),$$

wherein $\sigma$ represents the distance, $\lambda$ is a parameter value, (QC−QL) is a position error and (VC−VL) is a velocity error associated with commanded movement of the joint;
computing a sliding mode control action using a non-linear function of the distance to the sliding mode surface; and
causing the joint to be moved at least partially in response to the sliding mode control action.

11. The medical robotic system according to claim 10, wherein the controller is configured to compute a reaching law gain using the computed distance and compute the sliding mode control action based at least in part on a product of the reaching law gain and the computed distance.

12. The medical robotic system according to claim 11, wherein the controller is configured to compute a current state of an integrator using a prior state of the integrator and the computed distance, limit the product of the reaching law gain and the computed distance to be less than a maximum control action, and modify the current state of the integrator using the limited product so as to limit a sum of the product and the current state of the integrator to be less than the maximum control action, wherein the computation of the sliding mode control action is based at least in part on a sum of the limited product and the modified current state of the integrator.

13. The medical robotic system according to claim 10, wherein the controller is configured to filter the sliding mode control action to avoid abrupt changes when causing the joint to be moved.

14. The medical robotic system according to claim 10, wherein the controller is configured to dynamically limit the sliding mode control action using an acceleration factor derived from the commanded movement of the joint and cause the joint to be moved at least partially in response to the dynamically limited sliding mode control action.

* * * * *